United States Patent [19]
Sjøholm et al.

[11] Patent Number: 5,948,661
[45] Date of Patent: Sep. 7, 1999

[54] MYXOCOCCUS PEROXIDASE

[75] Inventors: Carsten Sjøholm; Iben Nørrevang, both of Allerød; Anders Hjelholt Pedersen, Lyngby, all of Denmark

[73] Assignee: Novo Nordisk A/S, Bagsvaerd, Denmark

[21] Appl. No.: 08/632,464

[22] PCT Filed: Oct. 26, 1994

[86] PCT No.: PCT/DK94/00393

§ 371 Date: Apr. 23, 1996

§ 102(e) Date: Apr. 23, 1996

[87] PCT Pub. No.: WO95/11964

PCT Pub. Date: May 4, 1995

[30] Foreign Application Priority Data

Oct. 26, 1993 [DK] Denmark ................................. 1200/93
Mar. 7, 1994 [DK] Denmark ..................................... 265
May 27, 1994 [DK] Denmark ..................................... 596

[51] Int. Cl.⁶ ........................................................ C12N 9/08
[52] U.S. Cl. ........................ 435/192; 435/189; 435/71.2; 424/94.4
[58] Field of Search ..................................... 435/192, 189, 435/71.2; 424/94.4

[56] References Cited

U.S. PATENT DOCUMENTS

| | | | |
|---|---|---|---|
| 4,698,306 | 10/1987 | Noda | 435/192 |
| 5,116,751 | 5/1992 | Shinmen et al. | 435/194 |
| 5,451,337 | 9/1995 | Liu et al. | 252/102 |

FOREIGN PATENT DOCUMENTS

| | | |
|---|---|---|
| 0 486 067 | 5/1992 | European Pat. Off. . |
| WO 89/09813 | 10/1989 | WIPO . |
| WO 91/05839 | 5/1991 | WIPO . |
| WO 91/05858 | 5/1991 | WIPO . |
| WO 92/18683 | 10/1992 | WIPO . |
| WO 94/12621 | 6/1994 | WIPO . |

OTHER PUBLICATIONS

Kato, et al., Plant Cell Physiol. vol. 26, No. 7, pp. 1291–1301 (1985).
Bergey' Manual of Systematic Bacteriology, vol. 3, Staley et al. ed., pp. 2139–2148, 1989.

*Primary Examiner*—Irene Marx
*Attorney, Agent, or Firm*—Steve T. Zelson, Esq.; Valeta Gregg, Esq.

[57] ABSTRACT

A purified peroxidase obtained from a strain of Myxococcus, having a molecular weight of about 40 kDA as determined by SDS-PAGE, which is stable up to 60° C. for 2 hours without loss of activity, and retains activity at pH 10.5.

3 Claims, 3 Drawing Sheets

MYXOCOCCUS PEROXIDASE

CROSS-REFERENCE TO RELATED APPLICATIONS

This application was filed under 35 USC 371 as the national phrase of PCT/DK94/00393 filed Oct. 26, 1994, which is incorporated herein by reference.

FIELD OF INVENTION

The present invention relates to a novel peroxidase, a process for its production and to its use in bleaching and detergent compositions.

BACKGROUND OF THE INVENTION

Peroxidases (E.C. 1.11.1.7) are enzymes that catalyze the oxidation of a substrate (an electron or hydrogen donor) with hydrogen peroxide. Such enzymes are known from microbial, plant and animal origins, e.g. peroxidase from *Coprinus cinereus* (cf. e.g. EP 179,486). They are typically hemoproteins, i.e. they contain a heme as a prosthetic group.

It has been found that peroxidases, utilizing hydrogen peroxide as substrate, are able to enhance the bleaching effect of hydrogen peroxide during washing. The use of peroxidases for bleaching stains on fabrics is described in WO 89/09813. It has also been found that coloured substances leached from dyed fabrics could be bleached by means of peroxidases together with hydrogen peroxide. The use of peroxidases for inhibiting dye transfer in this way is described in WO 91/05839.

Certain oxidizable substrates, e.g. metal ions and phenolic compounds such as 7-hydroxycoumarin (7HCm), vanillin (VAN), and p-hydroxybenzenesulfonate (pHBS), have been described as accelerators or enhancers, able to enhance bleaching reactions (cf. e.g. WO 92/18683, WO 92/18687, and Kato M and Shimizu S, Plant Cell Physiol. 1985 26 (7), pp. 1291–1301 (cf. Table 1 in particular). In WO 94/12621 other types of enhancing agents are disclosed, e.g. phenothiazines and phenoxazines.

It is the object of this invention to provide a peroxidase with improved bleaching performance at high pH.

SUMMARY OF THE INVENTION

We have unexpectedly found that a novel peroxidase can be obtained from Myxococcaceae, a family not previously reported to produce peroxidase, and we have further found that, surprisingly, this novel peroxidase shows excellent performance in bleaching assays at pH 10.5.

Accordingly, the invention provides a peroxidase preparation, characterized by being producible by cultivation of a peroxidase producing strain of the family Myxococcaceae.

The invention further provides a process for the production of peroxidase, characterized by comprising cultivation in a suitable nutrient medium of a peroxidase-producing strain of Myxococcaceae. Finally, the invention provides use of said peroxidase in bleaching and detergent compositions.

BRIEF DESCRIPTION OF DRAWINGS

The present invention is further illustrated by reference to the accompanying drawings, in which.

DETAILED DISCLOSURE OF THE INVENTION

Microorganism

Figure 1:
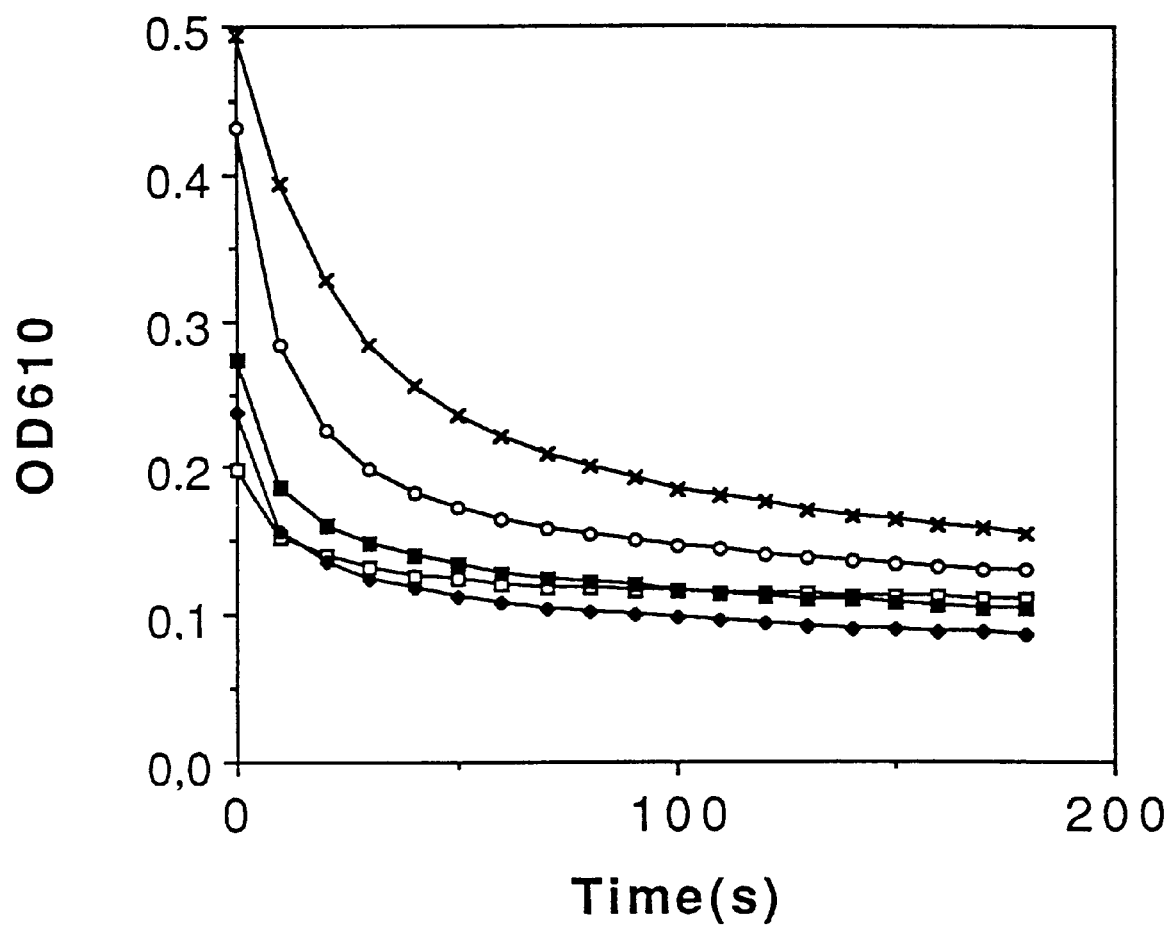
FIG. 1 shows the initial bleaching of Direct Blue 1 (DB1) under the following conditions: 100 μM $H_2O_2$; 20 mM acetate/phosphate-buffer; 0.12 PODU/ml *Myxococcus virescens* peroxidase; pH 5 (□)-pH 6 (♦)-pH 7 (■)-pH 8 (○)-pH 9 (X), respectively; room temperature.

According to the invention, peroxidase is derived from a peroxidase-producing strain of the Myxococcaceae. In the family Myxococcaceae the genera Myxococcus and Corallococcus are preferred, in particular *Myxococcus virescens, Myxococcus fulvus, Myxococcus xanthus, Corallococcus coralloides* and *Corallococcus exiguus.*

The family Myxococcaceae is described in Myxobacteria II (M. Dworkin and D. Kaiser, Eds.), American Society for Microbiology 1993.

A strain representative of *Myxococcus virescens* has been deposited according to the Budapest Treaty on the International Recognition of the Deposits of Microorganisms for the Purpose of Patent Procedures, on Oct. 4, 1993, at Deutsche Sammlung von Microorganismen und Zellkulturen GmbH Mascheroder Weg 1b, D-3300 Braunschweig, Germany, under Accession No. DSM 8593.

A strain representative of *Myxococcus fulvus* has been deposited according to the Budapest Treaty on the International Recognition of the Deposits of Microorganisms for the Purpose of Patent Procedures, on Feb. 9, 1994, at Deutsche Sammlung von Microorganismen und Zellkulturen GmbH, under Accession No. DSM 8969.

A strain representative of *Myxococcus xanthus* has been deposited according to the Budapest Treaty on the International Recognition of the Deposits of Microorganisms for the Purpose of Patent Procedures, on Feb. 9, 1994, at Deutsche Sammlung von Microorganismen und Zellkulturen GmbH, under Accession No. DSM 8970.

A strain representative of *Corallococcus coralloides* has been deposited according to the Budapest Treaty on the International Recognition of the Deposits of Microorganisms for the Purpose of Patent Procedures, on Feb. 9, 1994, at Deutsche Sammlung von Microorganismen und Zellkulturen GmbH, under Accession No. DSM 8967.

A strain representative of *Corallococcus exiguus* has been deposited according to the Budapest Treaty on the International Recognition of the Deposits of Microorganisms for the Purpose of Patent Procedures, on Feb. 9, 1994, at Deutsche Sammlung von Microorganismen und Zellkulturen GmbH, under Accession No. DSM 8968.

Production of Peroxidase

Peroxidase of the invention may be produced by aerobic cultivation of the above mentioned microbial strain on a nutrient medium containing suitable carbon and nitrogen sources, such media being known in the art. A temperature in the range of from 20 to 30° C. is suitable for growth and peroxidase production.

Alternatively, peroxidase of the invention can be produced by aerobic cultivation of a transformed host organism containing the appropriate genetic information from the above mentioned strain. Such transformants can be prepared and cultivated by methods known in the art.

The peroxidase can be recovered by :removing the cells from the fermentation medium (e.g. by centrifugation or filtration) and then concentrating the broth (e.g. by ultrafiltration). If desired, the peroxidase can be further purified by known methods.

Immunochemical Properties

Peroxidase preparations having immunochemical properties identical or partially identical to those of a peroxidase produced by a peroxidase producing strain of *Myxococcus virescens*, DSM 8593, or a peroxidase producing strain of *Myxococcus fulvus*, DSM 8969, or a peroxidase producing strain of *Myxococcus xanthus*, DSM 8970, or a peroxidase producing strain of *Corallococcus coralloides*, DSM 8967, or a peroxidase producing strain of *Corallococcus exiguus*, DSM 8968, are within the scope of the invention. The immunochemical properties can be determined immunologically by cross-reaction identity tests. The identity tests can be performed by the well-known Ouchterlony double immunodiffusion procedure or by tandem crossed immunoelectrophoresis according to I. M. Roitt; Immunology, Gower Medical Publishing (1985) and N. H. Axelsen; Handbook of Immunoprecipitation-in-Gel Techniques, Blackwell Scientific Publications (1983), Chapters 5 and 14. The terms "antigenic identity" and "partial antigenic identity" are described in the same book, Chapters 5, 10 and 20.

Thermostability

The thermostability of the peroxidase of the invention was investigated in the temperature interval of from room temperature to 90° C. The *Myxococcus virescens*, DSM 8593, peroxidase was stable up to 60° C. for 2 hours without loss of activity. However, at 90° C. all activity was lost after 15 min.

Bleaching

To obtain a bleaching effect of the Myxococcaceae peroxidase, hydrogen peroxide or a precursor of hydrogen peroxide, preferably perborate or percarbonate, or a hydrogen peroxide generating enzyme system, e.g. an oxidase and its substrate, or a peroxycarboxylic acid or a salt thereof, should be present in the bleaching composition of the invention as substrate for the peroxidase.

While the mechanism of peroxidase bleaching of coloured substances present on fabrics or in the wash liquor has not yet been elucidated, it is currently believed that the enzyme acts by reducing hydrogen peroxide and oxidizing the coloured substance (electron donor substrate), thereby either generating a colourless substance or providing a substance which is not adsorbed to the fabric. This reaction is shown in Reaction Scheme 1 below.

Reaction Scheme 1

Peroxidase
Donor substrate + $H_2O_2$ –> oxidized donor + $H_2O$

According to the invention, the peroxidase may typically be a component of a bleaching composition. In the bleaching composition, the amount of peroxidase corresponds to a concentration in the wash liquor of between 0.01 and 20 PODU/ml, and the amount of hydrogen peroxide or hydrogen peroxide precursor or hydrogen peroxide generating enzyme system or percarboxylic acid or a salt thereof corresponds to a hydrogen peroxide concentration of up to 20 mM $H_2O_2$, preferably a hydrogen peroxide concentration of up to 1 mM $H_2O_2$.

Determination of Peroxidase Activity

1 Peroxidase unit (PODU) is the amount of enzyme that catalyzes the conversion of 1 μmol hydrogen peroxide per minute at the following analytical conditions: 0.88 mM hydrogen peroxide, 1.67 mM 2,2'-azinobis (3-ethylbenzothiazoline-6-sulfonate), 0.1 M phosphate buffer, pH 7.0, incubated at 30° C., photometrically followed at 418 nm.

For use of the present peroxidase for bleaching purposes, it has been found that the addition of another oxidizable substrate (for the peroxidase of the invention) at the beginning or during the washing and/or rinsing process may enhance the bleaching effect of the peroxidase employed. This is thought to be ascribable to the formation of radicals or other oxidized states of this substrate which participate in the bleaching or other modification of the coloured substance. Examples of such oxidizable substrates are organic compounds such as phenolic compounds, e.g. p-hydroxybenzenesulfonate and 10-propionic acid phenothiazine and other phenothiazines and phenoxazines and derivatives thereof as described in WO 94/12621. The amount of oxidizable substrate corresponds to a concentration in the wash liquor of between 0.1 μM and 100 μM.

Detergent Compositions

In all the following detergent compositions hydrogen peroxide or a precursor of hydrogen peroxide, preferably perborate or percarbonate, or a hydrogen peroxide generating enzyme system, e.g. an oxidase and its substrate, or a peroxycarboxylic acid or a salt thereof, should be present as substrate for the peroxidase.

According to the invention, the peroxidase may typically be a component of a detergent composition. As such, it may be included in the detergent composition in the form of a non-dusting granulate, a stabilized liquid, or a protected enzyme. Non-dusting granulates may be produced, e.g., as disclosed in U.S. Pat. Nos. 4,106,991 and 4,661,452 (both to Novo Industri A/S) and may optionally be coated by methods known in the art. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in patent GB 1483591. Liquid enzyme preparations may, for instance, be stabilized by adding a polyol such as propylene glycol, a sugar or sugar alcohol, lactic acid or boric acid according to established methods. Other enzyme stabilizers are well known in the art. Protected enzymes may be prepared according to the method disclosed in EP 238,216.

The detergent composition of the invention may be in any convenient form, e.g. as powder, granules, paste or liquid. A liquid detergent may be aqueous, typically containing up to 70% of water and 0–30% of organic solvent, or nonaqueous.

The detergent composition comprises one or more surfactants, each of which may be anionic, nonionic, cationic, or zwitterionic. The detergent will usually contain 0–50% of anionic surfactant such as linear alkylbenzenesulfonate (LAS), alpha-olefin sulfonate (AOS), alkyl sulfate (fatty alcohol sulfate) (AS), alcohol ethoxysulfate (AEOS or AES), secondary alkanesulfonates (SAS), alpha-sulfo fatty acid methyl esters, alkyl- or alkenylsuccinic acid or soap. It may also contain 0–40% of nonionic surfactant such as alcohol (ethoxylate (AEO or AE), carboxylated alcohol ethoxylates, nonylphenol ethoxylate, alkylpolyglycoside, alkyldimethylamineoxide, ethoxylated fatty acid monoethanolamide, fatty acid monoethanolamide, or polyhydroxy alkyl fatty acid amide (e.g. as described in WO 92/06154).

The detergent composition may additionally comprise one or more other enzymes, such as amylase, lipase, cutinase, protease, cellulase, and/or another oxidoreductase.

The detergent may contain 1–65% of a detergent builder or complexing agent such as zeolite, diphosphate, triphosphate, phosphonate, citrate, nitrilotriacetic acid (NTA), ethylenediaminetetraacetic acid (EDtA), diethylenetriaminepentaacetic acid (DTMPA), alkyl- or alkenylsuccinic acid, soluble silicates or layered silicates (e.g. SKS-6 from Hoechst). The detergent may also be unbuilt, i.e. essentially free of detergent builder.

The detergent may comprise one or more polymers. Examples are carboxymethylcellulose ((CMC), poly(vinylpyrrolidone) (PVP), polyethyleneglycol (PEG), poly(vinyl alcohol) (PVA), polycarboxylates such as polyacrylates, maleic/acrylic acid copolymers and lauryl methacrylate/acrylic acid copolymers.

The detergent may contain a bleaching system which may comprise a $H_2O_2$ source such as perborate or percarbonate which may be combined with a peracid-forming bleach activator such as tetraacetylethylenediamine (TAED) (Dr nonanoyloxybenzenesulfonate (NOBS). Alternatively, the bleaching system may comprise peroxyacids of e.g. the amide, imides, or sulfone type.

The enzymes of the detergent composition of the invention may be stabilized using conventional stabilizing agents, e.g. a polyol such as propylene glycol or glycerol, a sugar or sugar alcohol, lactic acid, boric acid, or a boric acid derivative as e.g. an aromatic borate ester, and the composition may be formulated as described in erg. WO 92/19709 and WO 92/19708.

The detergent may also contain other conventional detergent ingredients such as e.g. fabric conditioners including clays, foam boosters, suds suppressors, anti-corrosion agents, soil-suspending agents, anti-soil redeposition agents, dyes, bactericides, optical brighteners, or perfume.

The pH (measured in aqueous solution at use concentration) will usually be neutral or alkaline, e.g. 7–11.

Particular forms of detergent compositions within the scope of the invention include:

1) A detergent composition formulated as a granulate having a bulk density of at least 600 g/l comprising

| | |
|---|---|
| linear alkylbenzenesulfonate (calculated as acid) | 7–12% |
| alcohol ethoxysulfate (e.g. $C_{12-18}$ alcohol, 1–2 EO) or alkyl sulfate (e.g. $C_{16-18}$) | 1–4% |
| alcohol ethoxylate (e.g. $C_{14-15}$ alcohol, 7 EO) | 5–9% |
| sodium carbonate (as $Na_2CO_3$) | 14–20% |
| soluble silicate (as $Na_2O,2SiO_2$) | 2–6% |
| zeolite (as $NaAlSiO_4$) | 15–22% |
| sodium sulfate (as $Na_2SO_4$) | 0–6% |
| sodium citrate/citric acid (as $C_6H_5Na_3O_7/C_6H_8O_7$) | 0–15% |
| sodium perborate (as $NaBO_3.H_2O$) | 11–18% |
| TAED | 2–6% |
| carboxymethylcellulose | 0–2% |
| polymers (e.g. maleic/acrylic acid copolymer, PVP, PEG) | 0–3% |
| enzymes | 0–5% |
| minor ingredients (e.g. suds suppressors, perfume, optical brightener, photobleach | 0–5% |

2) A detergent composition formulated as a granulate having a bulk density of at least 600 g/l comprising

| | |
|---|---|
| linear alkylbenzenesulfonate (calculated as acid) | 6–11% |
| alcohol ethoxysulfate (e.g. $C_{12-18}$ alcohol, 1–2 EO) or alkyl sulfate (e.g. $C_{16-18}$) | 1–3% |
| alcohol ethoxylate (e.g. $C_{14-15}$ alcohol, 7 EO) | 5–9% |
| sodium carbonate (as $Na_2CO_3$) | 15–21% |
| soluble silicate (as $Na_2O,2SiO_2$) | 1–4% |
| zeolite (as $NaAlSiO_4$) | 24–34% |
| sodium sulfate (as $Na_2SO_4$) | 4–10% |
| sodium citrate/citric acid (as $C_6H_5Na_3O_7/C_6H_8O_7$) | 0–15% |
| carboxymethylcellulose | 0–2% |
| polymers (e.g. maleic/acrylic acid copolymer, PVP, PEG) | 1–6% |
| enzymes | 0–5% |
| minor ingredients (e.g. suds suppressors, perfume) | 0–5% |

3) A detergent composition formulated as a granulate having a bulk density of at least 600 g/l comprising

| | |
|---|---|
| linear alkylbenzenesulfonate (calculated as acid) | 5–9% |
| alcohol ethoxylate (e.g. $C_{12-15}$ alcohol, 7 EO) | 7–14% |
| soap as fatty acid (e.g. $C_{16-22}$) | 1–3% |
| sodium carbonate (as $Na_2CO_3$) | 10–17% |
| soluble silicate (as $Na_2O,2SiO_2$) | 3–9% |
| zeolite (as $NaAlSiO_4$) | 23–33% |
| sodium sulfate (as $Na_2SO_4$) | 0–4% |
| sodium perborate (as $NaBO_3.H_2O$) | 8–16% |
| TAED | 2–8% |
| phosphonate (e.g. EDTMPA) | 0–1% |
| carboxymethylcellulose | 0–2% |
| polymers (e.g. maleic/acrylic acid copolymer, PVP, PEG) | 0–3% |
| enzymes | 0–5% |
| minor ingredients (e.g. suds suppressors, perfume, optical brightener) | 0–5% |

4) A detergent composition formulated as a granulate having a bulk density of at least 600 g/l comprising

| | |
|---|---|
| linear alkylbenzenesulfonate (calculated as acid) | 8–12% |
| alcohol ethoxylate (e.g. $C_{12-15}$ alcohol, 7 EO) | 10–25% |
| sodium carbonate (as $Na_2CO_3$) | 14–22% |
| soluble silicate (as $Na_2O,2SiO_2$) | 1–5% |
| zeolite (as $NaAlSiO_4$) | 25–35% |
| sodium sulfate (as $Na_2SO_4$) | 0–10% |
| carboxymethylcellulose | 0–2% |
| polymers (e.g. maleic/acrylic acid copolymer, PVP, PEG) | 1–3% |
| enzymes | 0–5% |
| minor ingredients (e.g. suds suppressors, perfume) | 0–5% |

5) An aqueous liquid detergent composition comprising

| | |
|---|---|
| linear alkylbenzenesulfonate (calculated as acid) | 15–21% |
| alcohol ethoxylate (e.g. $C_{12-15}$ alcohol, 7 EO or $C_{12-15}$ alcohol, 5 EO) | 12–18% |
| soap as fatty acid (e.g. oleic acid) | 3–13% |
| alkenylsuccinic acid ($C_{12-14}$) | 0–13% |
| aminoethanol | 8–18% |
| citric acid | 2–8% |
| phosphonate | 0–3% |
| polymers (e.g. PVP, PEG) | 0–3% |
| borate (as $B_4O_7$) | 0–2% |
| ethanol | 0–3% |
| propylene glycol | 8–14% |
| enzymes | 0–5% |
| minor ingredients (e.g. dispersants, suds suppressors, perfume, optical brightener) | 0–5% |

6) An aqueous structured liquid detergent composition comprising

| | |
|---|---|
| linear alkylbenzenesulfonate (calculated as acid) | 15–21% |
| alcohol ethoxylate (e.g. $C_{12-15}$ alcohol, 7 EO or $C_{12-15}$ alcohol, 5 EO) | 3–9% |
| soap as fatty acid (e.g. oleic acid) | 3–10% |
| zeolite (as $NaAlSiO_4$) | 14–22% |
| potassium citrate | 9–18% |
| borate (as $B_4O_7$) | 0–2% |
| carboxymethylcellulose | 0–2% |
| polymers (e.g. PEG, PVP) | 0–3% |
| anchoring polymers as e.g. lauryl methacrylate/acrylic acid copolymer; molar ratio 25:1; MW 3800 | 0–3% |
| glycerol | 0–5% |
| enzymes | 0–5% |
| minor ingredients (e.g. dispersants, suds suppressors, perfume, optical brighteners) | 0–5% |

7) A detergent composition formulated as a granulate having a bulk density of at least 600 g/l comprising

| | |
|---|---|
| fatty alcohol sulfate | 5–10% |
| ethoxylated fatty acid monoethanolamide | 3–9% |
| soap as fatty acid | 0–3% |
| sodium carbonate (as $Na_2CO_3$) | 5–10% |
| soluble silicate (as $Na_2O,2SiO_2$) | 1–4% |
| zeolite (as $NaAlSiO_4$) | 20–40% |
| sodium sulfate (as $Na_2SO_4$) | 2–8% |
| sodium perborate (as $NaBO_3.H_2O$) | 12–18% |

-continued

| | |
|---|---|
| TAED | 2–7% |
| polymers (e.g. maleic/acrylic acid copolymer, PEG) | 1–5% |
| enzymes | 0–5% |
| minor ingredients (e.g. optical brightener, suds suppressors, perfume) | 0–5% |

8) A detergent composition formulated as a granulate comprising

| | |
|---|---|
| linear alkylbenzenesulfonate (calculated as acid) | 8–14% |
| ethoxylated fatty acid monoethanolamide | 5–11% |
| soap as fatty acid | 0–3% |
| sodium carbonate (as $Na_2CO_3$) | 4–10% |
| soluble silicate (as $Na_2O,2SiO_2$) | 1–4% |
| zeolite (as $NaAlSiO_4$) | 30–50% |
| sodium sulfate (as $Na_2SO_4$) | 3–11% |
| sodium citrate (as $C_6H_5Na_3O_7$) | 5–12% |
| polymers (e.g. PVP, maleic/acrylic acid copolymer, PEG) | 1–5% |
| enzymes | 0–5% |
| minor ingredients (e.g. suds suppressors, perfume) | 0–5% |

9) A detergent composition formulated as a granulate comprising

| | |
|---|---|
| linear alkylbenzenesulfonate (calculated as acid) | 6–12% |
| nonionic surfactant, | 1–4% |
| soap as fatty acid | 2–6% |
| sodium carbonate (as $Na_2CO_3$) | 14–22% |
| zeolite (as $NaAlSiO_4$) | 18–32% |
| sodium sulfate (as $Na_2SO_4$) | 5–20% |
| sodium citrate (as $C_6H_5Na_3O_7$) | 3–8% |
| sodium perborate (as $NaBO_3.H_2O$) | 4–9% |
| bleach activator (e.g. NOBS or TAED) | 1–5% |
| carboxymethylcellulose | 0–2% |
| polymers (e.g. polycarboxylate or PEG) | 1–5% |
| enzymes | 0–5% |
| minor ingredients (e.g. optical brightener, perfume) | 0–5% |

10) An aqueous liquid detergent composition comprising

| | |
|---|---|
| linear alkylbenzenesulfonate (calculated as acid) | 15–23% |
| alcohol ethoxysulfate (e.g. $C_{12-15}$ alcohol, 2–3 EO) | 8–15% |
| alcohol ethoxylate (e.g. $C_{12-15}$ alcohol, 7 EO or $C_{12-15}$ alcohol, 5 EO) | 3–9% |
| soap as fatty acid (e.g. lauric acid) | 0–3% |
| aminoethanol | 1–5% |
| sodium citrate | 5–10% |
| hydrotrope (e.g. sodium toluenesulfonate) | 2–6% |
| borate (as $B_4O_7$) | 0–2% |
| carboxymethylcellulose | 0–1% |
| ethanol | 1–3% |
| propylene glycol | 2–5% |
| enzymes | 0–5% |
| minor ingredients (e.g. polymers, dispersants, perfume, optical brighteners) | 0–5% |

11) An aqueous liquid detergent composition comprising

| | |
|---|---|
| linear alkylbenzenesulfonate (calculated as acid) | 20–32% |
| alcohol ethoxylate (e.g. $C_{12-15}$ alcohol, 7 EO or $C_{12-15}$ alcohol, 5 EO) | 6–12% |
| aminoethanol | 2–6% |
| citric acid | 8–14% |
| borate (as $B_4O_7$) | 1–3% |
| polymer (e.g. maleic/acrylic acid copolymer, anchoring polymers as e.g. lauryl methacrylate/acrylic acid copolymer and CMC) | 0–3% |
| glycerol | 3–8% |
| enzymes | 0–5% |
| minor ingredients (e.g. hydrotropes, dispersants, perfume, optical brighteners) | 0–5% |

12) A detergent composition formulated as a granulate having a bulk density of at least 600 g/l comprising

| | |
|---|---|
| anionic surfactant (linear alkylbenzenesulfonate, alkyl sulfate, alpha-olefinsulfonate, alpha-sulfo fatty acid methyl esters, alkanesulfonates, soap) | 25–40% |
| nonionic surfactant (e.g. alcohol ethoxylate) | 1–10% |
| sodium carbonate (as $Na_2CO_3$) | 8–25% |
| soluble silicates (as $Na_2O, 2SiO_2$) | 5–15% |
| sodium sulfate (as $Na_2SO_4$) | 0–5% |
| zeolite (as $NaAlSiO_4$) | 15–28% |
| sodium perborate (as $NaBO_3.4H_2O$) | 0–20% |
| bleach activator (TAED or NOBS) | 0–5% |
| enzymes | 0–5% |
| minor ingredients (e.g. perfume, optical brighteners) | 0–3% |

13) Detergent formulations as described in 1)–12) where the content of linear alkylbenzenesulfonate - or a part of it - is substituted by alkyl sulfate ($C_{12}$—$C_{18}$).

14) Detergent formulations as described in 1)–13) which contain a stabilized or encapsulated peracid either as an additional component or as a substitute for already specified bleach systems.

15) Detergent compositions as described in 1), 3), 7), 9), and 12) wherein perborate is substituted for percarbonate.

16) Detergent compositions as described in 1), 3), 7), 9), and 12) which additionally contains a Manganese catalyst. The Manganese catalyst may e.g. be one of the compounds described in "Efficient manganese catalysts for low-temperature bleaching", Nature 369, 1994, pp. 637–639.

17) Detergent composition formulated as a nonaqueous detergent liquid comprising a liquid nonionic surfactant as e.g. linear alkoxylated primary alcohol, a builder system (e.g. phosphate), enzyme and alkali. The detergent may also comprise anionic surfactant and/or a bleach system.

It is at present contemplated that in the detergent composition of the invention, the peroxidase may be added in an amount corresponding to a concentration in the wash liquor of between 0.01 to 20 PODU/ml.

The present invention is further illustrated in the following examples which are not in any way intended to limit the scope of the invention as claimed.

EXAMPLE 1

The peroxidase preparations of the invention may be produced by the method described in this example.

The peroxidase producing strain, e.g. *Myxococcus virescens*, DSM 8593, is inoculated on "CY" agar plates containing the following composition:

| | |
|---|---|
| Casitone | 3 g |
| Yeast extract | 1 g |
| $CaCl_2.2H_2O$ | 1 g |
| Agar | 15 g |

Water ad 1000 ml, pH 7.2
Incubation for 2 weeks at 26° C.

The agar is cut into pieces and transferred aseptically to shake flasks, each containing 100 ml medium with the following composition:

| | |
|---|---|
| Casitone | 6 g |
| $CaCl_2.2H_2O$ | 0.5 g |
| $MgSO_4.7H_2O$ | 2 g |
| Vitamin-solution | 1 ml, | all four ingredients mixed in 1000 ml 25 mM HEPES (Sigma H 3375) buffer solution, pH 7.

The flasks are incubated on a rotary shaker at 250 rpm, 26° C., for 6 days.

Using the above described method a culture of *Myxococcus virescens*, DSM 8593, gave a fermentation result of 0.2 PODU/ml.

After separation of the solid material by centrifugation the peroxidase may be concentrated by ultrafiltration using a 10 kDa cut off membrane. The ultrafiltrated preparation of *Myxococcus virescens*, DSM 8593, had an activity of 2.9 PODU/ml.

EXAMPLE 2

The ultrafiltrated preparation described in Ex. 1 was used in a number of dye bleaching experiments, using the initial bleaching of Direct Blue 1 (DB1). FIG. 1 shows the bleaching of DB 1 under the following conditions:

100 μM $H_2O_2$ 20 mM acetate/phosphate-buffer 0.12 PODU/ml (*Myxococcus virescens* peroxidase)

pH 5 (□)-pH 6 (♦)-pH 7 (■)-pH 8 (O)-pH 9 (X), respectively;

room temperature the initial concentration of DB1 is adjusted to yield an $OD_{610}$=0.6.

Reagents were mixed in a 1 cm cuvette, and the bleaching was started by addition of hydrogen peroxide. The bleaching was detected spectrophotometrically at 610 nm, which is the absorption peak of this dye.

Figure 2:
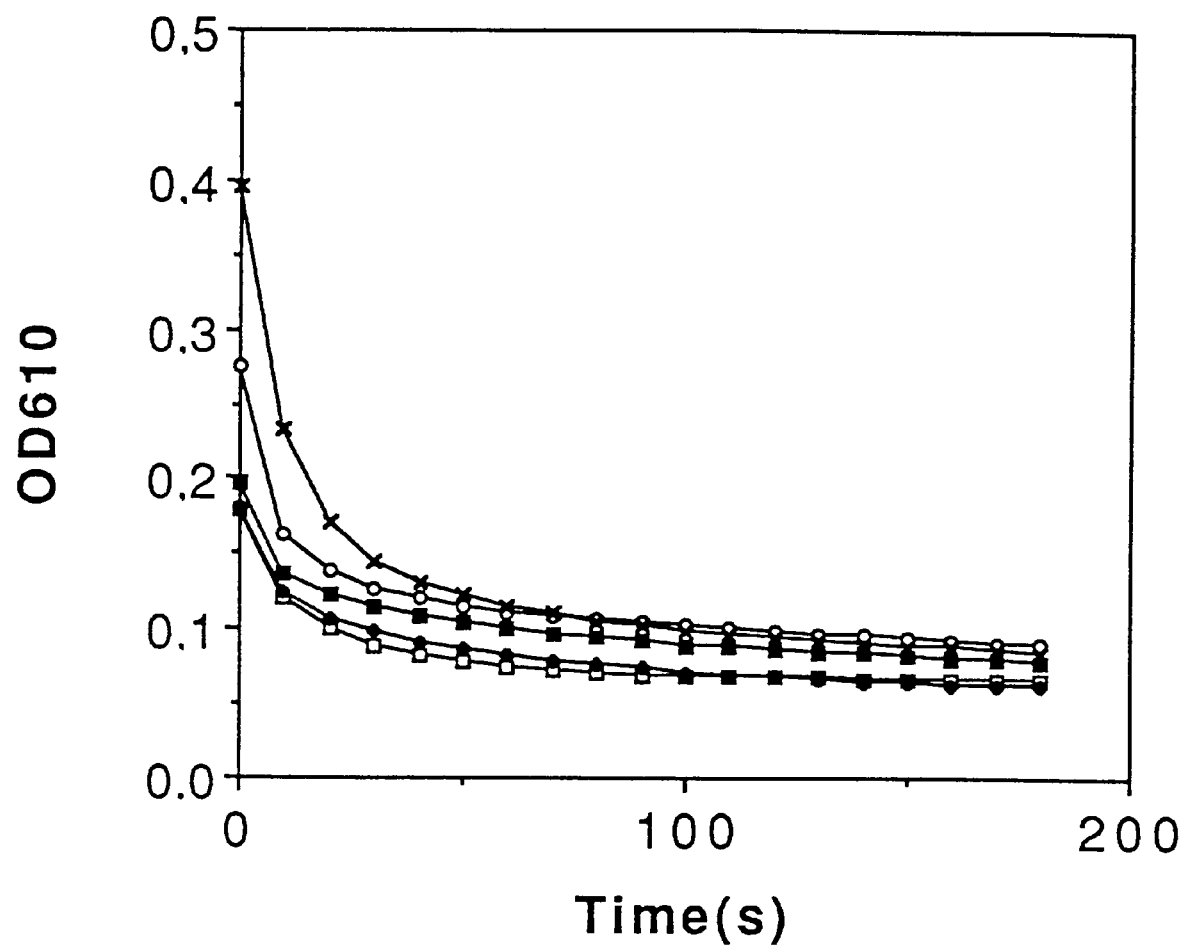
FIG. 2 shows the initial bleaching of DB1 using the conditions just described, but additionally containing 10 μM 10-propionic acid phenothiazine.

The same experiments were repeated using the conditions described above, but additionally containing an accelerator: 10 μM 10-propionic acid phenothiazine. The results are shown in FIG. 2.

The initial bleaching of Direct Blue 1 was also conducted at pH 10.5 (FIG. 3) with the following conditions:

100 μM $H_2O_2$ 25 mM Borate 0.5 PODU/ml (*Myxococcus virescens* peroxidase)

0 μM 10-propionic acid phenothiazine (□), 10 μM 10-propionic acid phenothiazine (♦), respectively room temperature the initial concentration of DB1 is adjusted to yield an $OD_{610}$ =0.6.

Figure 3:
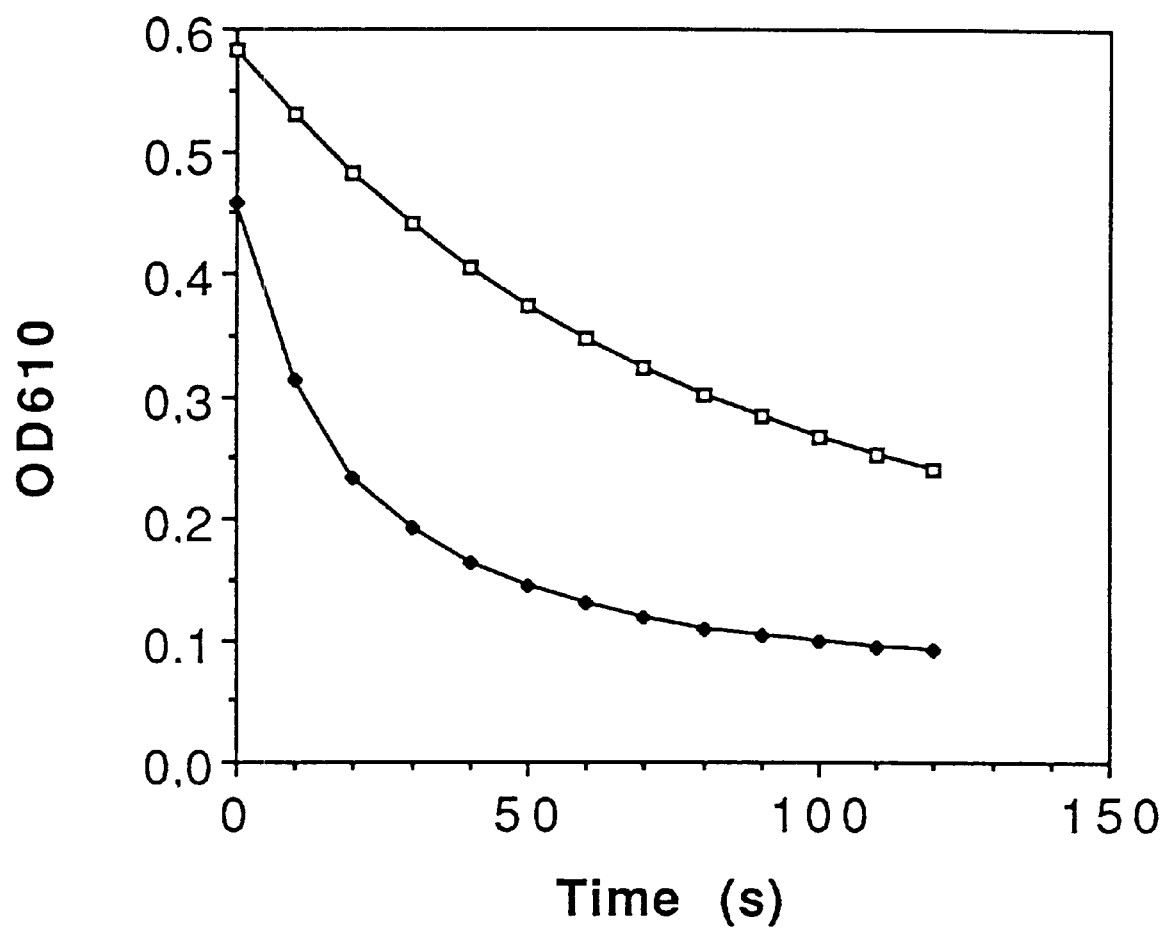
FIG. 3 shows the initial bleaching of DB1 at pH 10.5 under the following conditions: 100 μM $H_2O_2$; 25 mM Borate; 0.5 PODU/ml *Myxococcus virescens* peroxidase; 0 μM 10-propionic acid phenothiazine (□)/10 μM 10-propionic acid phenothiazine (♦), respectively; room temperature.

FIG. 3 shows that the effect of the accelerator is very pronounced at high pH. It also shows that the absorbance is reduced to at least half the initial value after 30 sec. in the experiment with 10 μM 10-propionic acid phenothiazine.

EXAMPLE 3

Purification of *Myxococcus virescens*

The ultrafiltrated preparation of M. virescens, DSM 8593, described in Example 1, was dialyzed against 20 mM NaAc pH 5.0 (hereafter called buffer A) and applied to a S-Sepharose Fast Flow column equilibrated with buffer A. The column was washed using three column volumes of buffer A and then eluted with a linear gradient from buffer A to Buffer A+0.15 M NaCl over 30 column volumes. Active fractions were collected and dialyzed against buffer A.

This material was applied to a Mono S column, and the column washed and eluted as described above. Active fractions were pooled and concentrated on an Amicon ultrafiltration cell. This pool was then applied to a Superose-12 column equilibrated with 0.1 M sodium phosphate buffer pH 6.

This procedure gave a substantially pure protein with a molecular weight as determined by SDS-PAGE (Pharmacia Phast system, operated according to instructions) of approx. 40 kDa.

We claim:

1. A purified peroxidase obtained from a strain of Myxococcus, which:

(a) has a molecular weight of about 40 kDA as determined by SDS-PAGE;

(b) is stable up to 60° C. for 2 hours without loss of activity; and (c) retains activity at pH 10.5, as determined in a Direct Blue 1 bleaching assay under the following conditions: 100 μM $H_2O_2$, 25 mM Borate, 10 μM 10-propionic acid phenothiazine, 0.5 PODU/ml Myxococcaceae peroxidase, at room temperature, wherein the initial concentration of DB1 is adjusted to yield an $OD_{610}$= 0.6.

2. The peroxidase of claim 1, wherein said strain is *Myxococcus virescens*.

3. The peroxidase of claim 2, wherein said strain is *Myxococcus virescens*, DSM 8593.

* * * * *